US008460279B2

(12) United States Patent
Vogler et al.

(10) Patent No.: US 8,460,279 B2
(45) Date of Patent: Jun. 11, 2013

(54) OPHTHALMIC LASER APPARATUS

(75) Inventors: Klaus Vogler, Eckental (DE); Christof Donitzky, Eckental (DE); Olaf Kittelmann, Berlin (DE)

(73) Assignee: Wavelight AG, Erlangen (DE)

( * ) Notice: Subject to any disclaimer, the term of this patent is extended or adjusted under 35 U.S.C. 154(b) by 1121 days.

(21) Appl. No.: 12/405,360

(22) Filed: Mar. 17, 2009

(65) Prior Publication Data
US 2010/0241107 A1 Sep. 23, 2010

(51) Int. Cl.
*A61B 17/22* (2006.01)
(52) U.S. Cl.
USPC .............................. 606/5; 351/160
(58) Field of Classification Search
USPC .............. 606/4–5, 11; 351/160, 205
See application file for complete search history.

(56) References Cited

U.S. PATENT DOCUMENTS

| 6,755,819 B1 * | 6/2004 | Waelti ............................... 606/5 |
| 2007/0027439 A1 | 2/2007 | Durrie et al. |
| 2008/0267814 A1* | 10/2008 | Bornstein ....................... 422/22 |

FOREIGN PATENT DOCUMENTS

| DE | 10206663 A1 | 8/2003 |
| EP | 1792593 A1 | 6/2007 |

OTHER PUBLICATIONS

Patent Cooperation Treaty—European Patent Office, "Notification of Transmittal of the International Search Report and the Written Opinion of the International Searching Authority, or the Declaration," International Application No. PCT/EP2009/001958, Sep. 30, 2009, 13 pages.

* cited by examiner

*Primary Examiner* — Victor Nguyen
(74) *Attorney, Agent, or Firm* — Haynes and Boone, LLP

(57) ABSTRACT

An ophthalmic laser apparatus includes components for providing a first pulsed laser beam (140) having beam properties matched to the ablation of corneal material and for providing a second pulsed laser beam (290) having beam properties matched to the making of an incision in the ocular tissue. The components include separate laser-sources (110, 130) for generating the two laser beams and also a plurality of optical elements which guide the two laser beams on separate beam paths to a respective beam exit location and focus them to a focal point situated outside the beam exit location. In accordance with the invention, the optical elements include an optical waveguide (250) serving for guidance of the second laser beam, at least the two laser-sources being accommodated in a common housing (340) and the optical waveguide extending within the housing at least over a part of its length.

20 Claims, 2 Drawing Sheets

OPHTHALMIC LASER APPARATUS

Figure 1:
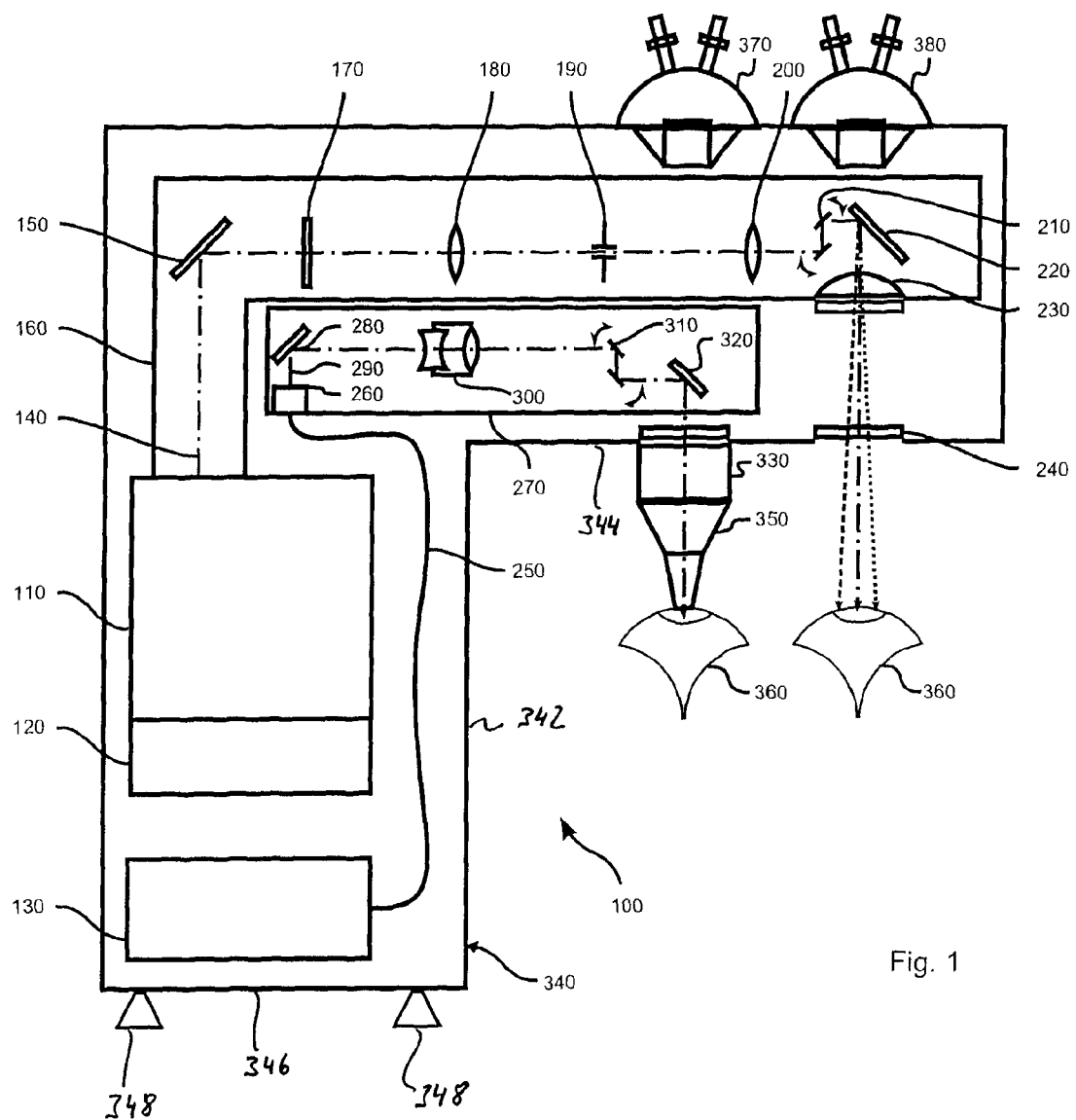

The invention relates to an ophthalmic laser apparatus.

In refractive ophthalmological surgery the refractive properties of the eye are changed by interventions in respect of the eye of a patient for the purpose of correcting sight defects. In this connection the so-called LASIK process (LASer In-situ Keratomileusis) has great importance, wherein firstly a flat corneal incision is made, as a result of which a small cover disc—the so-called flap—arises. The latter can be folded aside, in order to expose the underlying corneal tissue (stroma). Subsequently stromal tissue is resected (ablated) with a laser (normally an excimer laser) in accordance with an ablation profile ascertained for the individual patient. After this, the flap is folded back; the wound heals up relatively quickly.

The photoablation of corneal tissue is based on the destruction of the tissue material brought about by absorption of the radiant energy. The radiation wavelength employed for the ablation has to lie below the limit starting from which the corneal tissue becomes transmissive. In humans, this limit is around 300 nm. The prevalent ablation wavelength is the 193 nm of the ArF excimer laser. The thickness of ablation brought about per pulse is extremely small and lies, for example, in the region of tenths of micrometres.

For the purpose of making the flap incision in the course of LASIK, the mechanical microkeratome used formerly has recently been replaced by an fs laser—that is to say, a laser that generates pulsed laser radiation with pulse durations within the femtosecond range. For an intra-tissue incision, the laser radiation has to lie within the transmissive wavelength range of the cornea—that is to say, above approximately 300 nm. At the same time, the power density in the beam focus has to be great enough in order to generate an optical breakthrough, the so-called photodisruption. The effective region thereof is locally restricted to the focus diameter. In order to produce a planar incision, the beam focus must therefore be moved in succession, or in accordance with a different scan pattern, onto a plurality of closely adjacent points in the desired incision surface (incision plane).

At present, instrument systems with an excimer laser are employed for the correction of visual deficiencies, whereby further separate individual instruments assist, for instance for diagnostics, for surveying, or for making incisions. All these add-on instruments have to be placed in the surround field of the excimer laser, in order to be able to perform the operation swiftly and without complicated changes of position of the patient.

Previous practice in hospitals and in doctors' surgeries has conventionally provided the use of two separate laser systems: an excimer laser for the ablation and an fs laser for making incisions. The two laser systems are set up close together in the same room and can, for example, be reached by means of a swivelling or displaceable patient bed which permits the patient to be moved from one system to a position beneath the other. This makes the implementation of an operation consisting of a laser incision and a photoablation agreeable for the patient, insofar as he/she only has to lie down once and does not have to move actively between the partial operations, or even stand up.

As an alternative to a movement of the patient bed, in the state of the art a solution has become known wherein the fs laser system is equipped with a mobile articulated mirror arm. The patient is positioned with his/her eye to be treated beneath the beam exit window of the ablation laser system. The articulated mirror arm can be swivelled into the region between the eye and the beam exit window, in order—for example, in the course of LASIK—to be able to perform the initial flap incision in this way. Subsequently the articulated mirror arm is swivelled back, so that the eye is free for the treatment with the ablation laser beam. A disadvantageous aspect of such solutions with an articulated mirror arm is the limited precision in connection with the guidance of the laser beam, since in each position of the arm differing tolerance chains arise out of the precision of the adjustment of the individual mirrors.

For the purpose of reducing the size of an instrument system that is suitable both for corneal ablation and for intracorneal incisions, one could conceive of obtaining the UV radiation needed for the ablation and the fs radiation needed for the corneal incision from one and the same source of laser radiation, so that one makes do with a single source. For example, the UV radiation could be generated from an IR ground wave by frequency conversion. However, the frequency converters that are needed for this exhibit relatively high instability and unreliability, particularly in the case of conversion to wavelengths in the UV region below 300 nm, specifically by reason of the inherent compromises that have to be entered into in order to realise two or more wavelengths with the target parameters sufficient for the application. Each individual wavelength can only be generated sub-optimally. Consequently, in most cases the aggregate efficiency of the overall instrument is poor, and a relatively large amount of electrical energy has to be fed in. As a result, the cooling becomes costly, and the instrument becomes correspondingly large. Consequently the advantage of needing only a single instrument instead of two is also greatly diminished.

Moreover, methods have become known in the state of the art that permit refractive treatments of the eye to be carried out solely with an fs laser. An example in this respect is corneal lenticle extraction, wherein by means of the fs laser a lenticle (lens-shaped small disc) situated totally within the corneal tissue is cut free which is subsequently taken out by means of a lateral incision in the cornea. This lateral incision may, if desired, also be made with the fs laser. With these solutions an additional excimer laser for the ablation is not necessary. However, because in the case of the laser-induced optical breakthrough the focus dimensions determine the magnitude of the disruption, in the case of purely fs-based refractive treatment methods the same high precision of correction as in the case of ablation cannot be attained, at least at present.

The object of the invention is to create an ophthalmic laser apparatus that is suitable both for corneal ablation and for incisions, that can be constructed in the form of a comparatively compact instrument, that requires as few as possible changes of relative position of patient and instrument during an operation, and that permits both ablating and cutting laser treatment with, in each instance, optimally adapted radiation parameters.

For the purpose of achieving this object, the invention provides an ophthalmic laser apparatus including components for providing a first pulsed laser beam having beam properties matched to the ablation of corneal material and for providing a second pulsed laser beam having beam properties matched to the making of an incision in the ocular tissue, the components including separate laser-sources for generating the two laser beams and also including a plurality of optical elements which guide the two laser beams on separate beam paths to a respective beam exit location and focus them to a focal point situated outside the beam exit location. In accordance with the invention, the optical elements include an optical waveguide serving for guidance of the second laser beam, at least the two laser-sources being accommodated in a common housing, and the optical waveguide extending within the housing at least over a part of its length.

By virtue of the separation of the beam paths of the two laser beams and the simultaneous realisation of at least a part of the beam path of the second laser beam by means of an optical waveguide, a high degree of integration can be achieved. This permits a comparatively low-volume design. The provision of separate beam paths for the two laser beams permits, furthermore, a beam-guidance concept for each beam path to be developed and employed that is optimised with respect to the properties of the beam emission. No complicated optics—for example, dichroic optics or optics provided with dual HR coatings (HR=highly reflective)—have to be used for the purpose of guiding radiation from completely different spectral regions, such as is necessary, for example, in the case of solutions with a common radiation-source and with an at least partly common beam path. By virtue of the use of two separate laser-sources, the optimal beam quality for the respective desired therapeutic purpose can be made available without increased expenditure on energy/cooling. Depending on the particular application or degree of integration, in addition the emission of the second laser beam may occur at a stationary point in the laser apparatus or may be capable of being moved flexibly to various locations with the aid of the optical waveguide. In particular, the use of an optical waveguide allows a simple and space-saving integration of the laser-source for the second laser beam into the laser apparatus.

According to a preferred embodiment, the first laser-source is an excimer laser and the second laser-source is a fibre laser. Fibre lasers are capable of offering a comparatively high beam quality (typically with a beam-parameter product $M^2 \leq 1.3$) with very compact design. The high efficiency of fibre lasers—which amounts to, for example, around 30%—increases the electrical power consumption of the overall instrument only insignificantly. For example, by virtue of the fibre laser the power consumption may increase by only as little as, at most, 150 Watt in comparison with a laser apparatus that has only an ablation laser.

One possible way of arranging the two laser-sources in the housing provides that the second laser-source is arranged in the housing beneath the first laser-source, the optical waveguide being guided upwards within the housing from the second laser-source laterally past the first laser-source. The housing may exhibit a base part, which is provided for the purpose of mounting on a horizontal mounting surface (e.g. a floor) and which includes a bottom of the housing, and also a housing arm projecting transversely from the base part at a vertical distance from the bottom of the housing. In this case it is preferred that the two laser-sources are accommodated, at least mainly, in the base part of the housing, and at least some of the optical elements are accommodated in the housing arm. The beam paths of the two laser beams accordingly extend at least partly through the housing arm. For a contact area of the housing that is as small as possible, it is advisable to arrange the two laser-sources above one another, for which purpose one or more false bottoms, for example, may be present in the base part of the housing, onto which the various laser-sources may be placed.

Preferentially incorporated into the housing arm is a first beam tube which guides the first laser beam, which is expediently flushed with an inert gas (e.g. nitrogen), and which, inter alia, may contain a beam homogeniser, a scanner and also at least one focusing lens for focusing the first laser beam to a focal point situated outside the housing. In this case at least a part of the beam path of the second laser beam extends within the housing arm outside the first beam tube. In addition, an exit window for the first laser beam is formed on the housing arm.

According to one embodiment, a second beam tube extending along the first beam tube may be incorporated within the housing arm, through which the beam path of the second laser beam extends. In this case the optical waveguide extends within the housing between the second laser-source and the second beam tube.

At a distance upstream or downstream of the exit window for the first laser beam in the longitudinal direction of the arm the housing arm may bear focusing optics for the second laser beam. The focusing optics are preferably constructed in the form of an f-theta objective.

According to one variant, the optical waveguide may be guided out of the housing and may terminate in a handpiece, equipped at least with a scanner and with focusing optics, for application of the second laser beam. In this case the handpiece is expediently connected to the housing solely by one or more flexible cables, one of which contains the optical waveguide. In addition to the optical waveguide, in the at least one cable there may also extend, for example, an electrical power supply, a suction line as well as one or more data lines. Within the scope of the mobility of the at least one cable, the handpiece itself is capable of being positioned independently of the housing and the components, fitted therein or thereon, of the laser apparatus according to the invention. The size and shape of the handpiece are expediently such that the handpiece can be comfortably grasped with one hand and brought up to the eye to be treated, in order to make an incision in the ocular tissue there with the second laser beam emitted via the handpiece.

The optical waveguide may be guided out of the housing at a point that is situated on the housing arm at a distance upstream or downstream of the exit window for the first laser beam in the longitudinal direction of the arm.

In addition to a scanner and focusing optics, the handpiece may additionally contain a pulse compressor for time-compression of the pulses of the second laser beam, the pulse compressor preferentially exhibiting an optical miniature grating, for instance a transmission grating or a photonic crystal fibre (PCF).

The handpiece may be constructed with coupling structures that permit a mechanical coupling of the handpiece onto an eye to be treated or onto a suction ring placed onto the eye. In this way, a defined referencing of the focus location of the second laser beam in the direction of beam propagation in relation to the eye to be treated can be achieved. The coupling structures may, for example, include an adapter which is permanently or detachably fitted to the handpiece and which is capable of being brought, where appropriate, into suction-force-assisted coupling abutment with a suction ring which has already previously been placed on the eye.

The scanner that is provided in the handpiece is, for example, constituted by an electro-optical crystal with which the second laser beam can be spatially controlled. Electro-optical crystals of such a type are ordinarily based on the Pockels effect or Kerr effect, wherein as a result of application of an electric field to the crystal the optical properties thereof—such as, for example, the refractive index—are changed. Acousto-optical modulators may also bring about rapid controllable beam deflections by virtue of the induced Bragg grating. Alternatively, the scanner that is present in the handpiece may be, for example, an electro-optical hologram which is produced by recording a volume-phase hologram in a liquid crystal-monomer mixture and which generates efficient and controllable beam deflections by virtue of external electrical voltages.

On the other hand, a mirror scanner operating in accordance with the galvanometer principle, with two mirrors arranged so as to be capable of being tilted about mutually perpendicular axes, preferentially serves for scanning of the first laser beam. However, it will be understood that, if desired, other scanning principles may also come into operation for the scanning of the first laser beam.

The laser pulses generated by the second laser-source preferably have a pulse duration within the femtosecond range, in which case a pulse-stretcher for time-stretching of the laser pulses to pulse lengths longer than one picosecond may be connected between the second laser-source and the optical waveguide. The pulse stretching permits a lowering of the intensity of the laser pulses. This, in turn, results in a lower loading of the optical waveguide.

The optical waveguide may be, for example, a photonic crystal fibre (PCF) or a transmission fibre having a large modal field. Suitable LMA fibres have, for example, a core diameter from 20 μm to over 40 μm. By reason of the distribution of the light output over a larger area and by reason of the simultaneous relaying in low modal order or in the fundamental mode, LMA fibres permit a transmission of the radiation emitted by the second laser-source without impairing the beam parameters or destroying the LMA fibre by excessively high intensities. By virtue of large core diameters, or in the case of design in the form of hollow conductors, PCF fibres likewise permit high power transmissions. They are a different fibre-type from LMA fibres and are based not on total reflection but rather on the photonic bandgap effect.

It may be an advantage if at least a portion of the optical waveguide brings about a temporal pulse compression of the laser pulses of the second laser beam. This enables a still more compact structure of the laser apparatus than with standard compression gratings. The compression of the laser pulses which is otherwise to be implemented in a separate structural element (e.g. a compression grating) can consequently be shifted to the flexible optical waveguide; compression components outside the optical waveguide may accordingly be dispensed with.

A particularly preferred embodiment in this respect provides that at least the portion of the optical waveguide bringing about the pulse compression is constituted by a photonic hollow-core fibre. This type of PCF fibre designates a microstructured optical fibre which in the core region or in the sheath region typically contains fine capillary structures filled with air or with a gas. By variation of the hole-centre distances and of the diameters of the capillary structures, the optical parameters of the fibre and the properties of the light guidance can be controlled. In particular, a pulse compression of the laser pulses of the second laser beam can be obtained in this way.

The invention permits the integration of an fs laser for the generation of an intra-tissue incision, and of an excimer laser for the ablation of the cornea in an overall instrument, whereby the two lasers can be operated with their parameters that are optimal for the respective application. No compromises or mutually conflicting optimisations are necessary such as are unavoidable in the case of solutions with frequency converters which generate various wavelengths from a single source of laser radiation. Therefore the laser apparatus according to the invention permits, to the same extent, optimal results of treatment to be achieved such as are possible with specially tailor-made individual instruments. The use of a fibre laser for the second laser-source permits a simple integration without substantial additional space requirement. The use of a flexible optical waveguide for guiding the laser beam generated by the fibre laser offers high design flexibility in the case where the components of the laser apparatus according to the invention are accommodated in one housing.

In an embodiment of the laser apparatus in which the second laser beam is capable of being applied via a handpiece, the guidance of the second laser beam is expediently effected over the entire distance from the second laser-source as far as the handpiece via a flexible optical waveguide. In the handpiece, or already upstream thereof along the optical waveguide, a temporal pulse compression is then effected of the laser pulses which have been stretched into the picosecond range prior to being fed into the optical waveguide and which originally had a pulse duration within the fs range. In addition, in the handpiece a two-dimensional deflection of the second laser beam is expediently effected with the aid of suitable optical miniature structural elements. The handpiece, which may also be designated as a manual applicator, may have been adapted to the concrete application by virtue of its special design. In particular it is conceivable to realise interchangeable handpieces or handpiece inserts which, for example, may be capable of being attached, via a mechanically detachable interface, to a cable containing the optical waveguide. Hence the laser apparatus according to the invention may be employed for further fs laser applications in respect of the eye that go beyond the flap incision of LASIK.

The invention will be elucidated in more detail in the following on the basis of the appended drawings.

Figure 2:
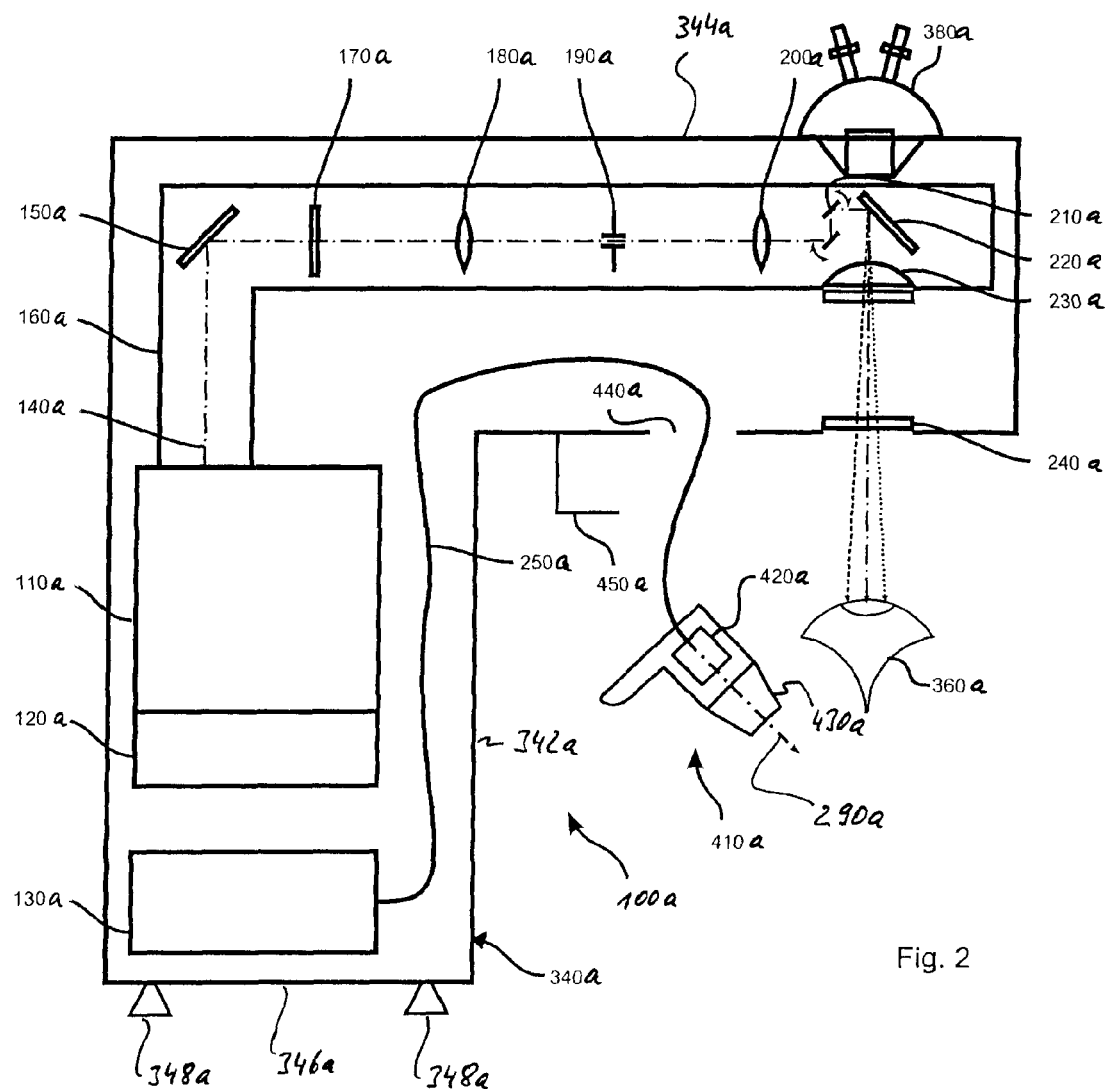

Represented are:

FIG. 1 schematically, a first exemplary embodiment of a laser apparatus according to the invention and FIG. 2 schematically, a second exemplary embodiment of a laser apparatus according to the invention.

The laser apparatus according to the exemplary embodiment shown in FIG. 1 takes the form of an integral ophthalmological laser-surgery system 100 which is suitable, in particular, for refractive eye treatments that serve for the elimination of visual deficiencies of an eye 360 to be treated. The laser-surgery system 100 includes an excimer laser 110 constituting a first laser-source, which generates a pulsed laser beam 140 having a UV wavelength. For example, the excimer laser is an ArF excimer laser which radiates at 193 nm. Assigned to the excimer laser 110 are control electronics 120 with appropriate control software and operating software.

By way of further laser-source, the laser-surgery system 100 includes an fs laser 130 which preferentially takes the form of a fibre laser and generates pulsed laser radiation with pulse durations within the femtosecond range. For example, the pulse duration of the laser pulses generated by the fs laser 130 lies between 100 fs and 800 fs; the wavelength of the laser radiation generated by the fs laser 130 lies, for example, in the NIR region, for instance between 1020 nm and 1070 nm, for example 1064 nm.

The laser beam 140 generated by the excimer laser 110 is guided in a beam tube (beamline) 160 which is flushed, in a manner not represented in any detail, with nitrogen or with another inert gas. Incorporated into the beam tube 160 are, inter alia, a passive deflecting mirror 150 which, in the exemplary case that is shown, deflects the laser beam 140 by an angle of 90°, a subsequent homogeniser 170 for smoothing the cross-section of the beam and reducing any intensity peaks, a beam-shaping arrangement consisting of a lens 180, an aperture 190 and a further lens 200, in order to cut a defined part out of the homogenised laser beam, a scanner 210 which is constituted here by a galvanometrically controlled pair of mirrors, a further passive deflecting mirror 220 and also a focusing lens 230 for focusing the laser beam 140. The laser beam 140 emerges from the beam tube 160 at the focusing lens 230 and is emitted to the outside through a transmission window 240.

In the beam path of the laser beam—denoted by 290—generated by the fs laser-source 130 there are situated in series a transmission fibre 250, a compression unit 260, a passive deflecting mirror 280, a telescope (beam expander) 300 serving for beam expansion, a scanner 310, a further passive deflecting mirror 320 and also a multi-lens, as a rule, f-theta objective 330 for focusing the laser beam 290. The compression unit 260 serves for time-compression of the laser pulses of the second laser beam 290, which previously were temporally stretched and amplified by means of a pulse-stretcher not represented in any detail and connected upstream of the transmission fibre 250. In the exemplary case of FIG. 1, the compression unit 260 is shown immediately following the transmission fibre 250. It Will be understood that the compression unit 260 may also be arranged at a different place within the part of the beam path of the second laser-source 290 adjoining the transmission fibre 250, for example upstream or downstream of the deflecting mirror 320. The compression unit 260 may be a transmission grating which compresses the laser pulses stretched into the picosecond range by means of the aforementioned pulse-stretcher to pulse durations of, for example, 500 fs or shorter. The compression unit 260 may also be omitted if the transmission fibre 250 is constituted by a PCF fibre having inherently pulse-compressing properties. Instead of a PCF fibre, an LMA fibre may also be used for the transmission fibre 250, dispensing, of course, with an inherent pulse compression within the fibre.

The scanner 310 may, just like the scanner 210, be constituted by a pair of galvanometrically actuated deflecting mirrors. Alternatively, it may be constituted, for example, by an electro-optical crystal that is sufficiently transmissive at the wavelength being used of the second laser beam 290.

In the exemplary case of FIG. 1 which is shown, the transmission fibre 250 extends between the fs laser 130 and a further beam tube 270 in which the compression unit 260, the deflecting mirrors 280, 320, the telescope 300 and also the scanner 310 are accommodated. As a rule, the beam tube 270 requires no flushing by an inert gas.

For the purpose of configuring the laser-surgery system 100 as a combination instrument, it has a housing 340 with a base part 342 and with a housing arm 344 attached to the top of the base part 342 and protruding laterally. The base part 342 of the housing 340 includes a housing bottom 346, on the underside of which preferentially vertically adjustable mounting feet 348 are accommodated, by means of which the laser-surgery system 100 can be mounted on the floor or on another horizontal mounting surface. The excimer laser 110, the associated control electronics 120 thereof and also the fs laser 130 are jointly accommodated in the base part 342 of the housing 340, the two lasers 110, 130 being arranged in superjacent planes and, in the exemplary case that is shown, the excimer laser 110 being arranged above the fs laser 130. The transmission fibre 250 is guided laterally upwards past the excimer laser 110 and the control electronics 120 arranged beneath said laser and is connected to the beam tube 270. The latter extends, just like the beam tube 160, into the housing arm 344 and extends in the longitudinal direction of the arm just beyond the focusing objective 330 which is suspended on the housing arm 344, if desired in weight-compensated manner. In the exemplary case that is shown, the beam tube 160 extends above the beam pipe 270 into the housing arm 344 and reaches beyond the beam tube 270 in the longitudinal direction of the arm, so that the laser beam 140 emerging from the focusing lens 230 can get past the beam tube 270 to the transmission window 240 and from there can emerge from the housing arm 344. It will be discerned that the exit-points of the two laser beams 140, 290 from the laser-surgery system 100 are situated in series at a distance in the longitudinal direction of the arm. By slight lateral displacement of a patient bed (not represented in any detail) which is set up underneath the housing arm 344, the eye 360 to be treated of the patient lying on the bed can consequently be optionally positioned beneath the transmission window 240 or beneath the focusing objective 330. It will be understood that, alternatively, the beam tube 270 may be arranged above the beam tube 160 in the housing 340. In this case the beam tube 270 reaches beyond the beam tube 160 in the longitudinal direction of the housing arm 344; the arrangement of the transmission window 240 and of the focusing objective 330 is then transposed accordingly.

For the purpose of precise referencing of the laser-surgery system 100 in relation to the eye 360, in the course of implementation of an incision by means of the fs laser beam 290 a patient interface 350 is fitted or capable of being fitted to the focusing objective 330 on the underside, which in turn is capable of being brought into coupling engagement with a suction ring (not represented in any detail) placed onto the eye 360 and held firmly there by suction force, or itself exhibits such a suction ring.

For the purpose of monitoring the progress and outcome of the operation, in the exemplary case that is shown the laser-surgery system 100 is provided with two microscopes 370, 380 which are fitted to the housing arm 344 and are situated substantially directly above the focusing objective 330 and the transmission window 240, respectively. In order to enable an observation of the eye 360, the deflecting mirrors 220, 320 are of dichroic design, having a high reflectivity in respect of the wavelength of the laser beam in question but, at the same time, being strongly transmissive in respect of the visual spectral region.

In the variant according to FIG. 2, identical or identically-acting components are provided with reference symbols identical to those in FIG. 1 but supplemented by a lower-case letter. For the purpose of avoiding unnecessary repetition, reference is made to the above elucidations relating to the exemplary embodiment shown in FIG. 1, unless otherwise stated below.

The laser-surgery system 100a according to FIG. 2 differs from the exemplary embodiment shown in FIG. 1 pre-eminently in that although the transmission fibre 250a is guided upwards past the excimer laser 110a into the region of the housing arm 344a it is then guided outwards out of the housing arm 344a at an exit-point 440a and terminates in a handpiece denoted generally by 410a. At least the part of the transmission fibre 250a extending outside the housing is expediently guided in a connecting cable which is not represented in any detail and in which additionally, for example, a suction line as well as electrical leads may also be guided. It will be understood that the various leads and also the transmission fibre 250a may be distributed to several connecting cables.

Integrated into the handpiece 410 are various optical components which perform at least the functions of beam deflection and beam focusing and, if desired, may also accomplish a temporal pulse compression and a beam expansion. The corresponding components are expediently constructed as miniature components, in which case, for reasons of space, an electro-optical crystal, for example, is suitable for the beam deflection. The optical components accommodated in the handpiece 410 are indicated schematically in FIG. 2 by a module 420*a*; of course, they may have been integrated into the handpiece 410*a* in the form of miniaturised individual components. The handpiece 410*a* further exhibits a patient interface 430*a* which serves for coupling the handpiece 410*a* onto the eye 360*a* or onto a suction ring seated on the eye. Besides the making of intracorneal incisions, in particular in the course of LASIK, with the handpiece 410*a*, cataract treatments or glaucoma treatments are also conceivable, for example, as possible applications.

Also indicated schematically in FIG. 2 is a stowage shelf 450, on which the handpiece 410*a* can be placed when not in use.

The invention claimed is:

1. An ophthalmic laser apparatus for ablation of corneal material and cutting of ocular tissue of the living eye, the apparatus comprising components for providing a first pulsed laser beam having first beam properties matched to the ablation of corneal material and for providing a second pulsed laser beam having second beam properties matched to the making of an incision in the ocular tissue, the components including separate laser-sources for generating the two laser beams and also a plurality of optical elements which guide the two laser beams on separate beam paths to a respective beam exit location and focus them to a focal point situated outside the beam exit location, wherein the optical elements include an optical waveguide serving for guidance of the second laser beam, in that at least the two laser-sources are accommodated in a common housing, and in that the optical waveguide extends within the housing at least over a part of its length;
   wherein the first laser-source is an excimer laser and the second laser-source is a fibre laser,
   wherein the second laser-source is arranged in the housing beneath the first laser-source and the optical waveguide is guided upwards within the housing from the second laser-source laterally past the first laser-source,
   wherein the housing exhibits a base part, provided for the purpose of mounting on a horizontal mounting surface and including a bottom of the housing, and a housing arm projecting transversely from the base part at a vertical distance from the bottom of the housing, and in that the two laser-sources are accommodated preferentially above one another at least mainly in the base part of the housing and at least some of the optical elements are accommodated in the housing arm.

2. The laser apparatus according to claim 1, wherein a first beam tube guiding the first laser beam flushed with an inert gas is incorporated into the housing arm, in that at least a part of the beam path of the second laser beam extends within the housing arm outside the first beam tube, and in that an exit window for the first laser beam is formed on the housing arm.

3. The laser apparatus according to claim 2, wherein a second beam tube extends along the first beam tube within the housing arm, and includes a portion of the beam path of the second laser beam, and in that the optical waveguide extends within the housing between the second laser-source and the second beam tube.

4. The laser apparatus according to claim 3, wherein the housing arm includes focusing optics for the second laser beam at a distance upstream or downstream of the exit window for the first laser beam in the longitudinal direction of the arm.

5. The laser apparatus according to claim 2, wherein the optical waveguide in guided out of the housing and terminates in a handpiece, equipped at least with a scanner and with focusing optics, for application of the second laser beam, the handpiece being connected to the housing solely by one or more flexible cables, one of which contains the optical waveguide.

6. The laser apparatus according to claim 5, wherein the optical waveguide is guided out of the housing at a point which is situated on the housing arm at a distance upstream or downstream of the exit window for the first laser beam in the longitudinal direction of the arm.

7. The laser apparatus according to claim 5, wherein the handpiece contains a pulse compressor for time-compression of the pulses of the second laser beam, the pulse compressor preferentially exhibiting an optical grating, for example a transmission grating.

8. The laser apparatus according to claim 5, wherein the handpiece is constructed with coupling structures which permit a mechanical coupling of the handpiece onto an eye to be treated or onto a suction ring placed onto the eye.

9. The laser apparatus according to claim 1, wherein the optical waveguide includes a photonic transmission fibre having a large modal field.

10. The laser apparatus according to claim 9, wherein at least a portion of the optical waveguide brings about a temporal pulse compression.

11. An ophthalmic laser apparatus for ablation of corneal material and cutting of ocular tissue of the living eye, the apparatus comprising components for providing a first pulsed laser beam having first beam properties matched to the ablation of corneal material and for providing a second pulsed laser beam having second beam properties matched to the making of an incision in the ocular tissue, the components including separate laser-sources for generating the two laser beams and also a plurality of optical elements which guide the two laser beams on separate beam paths to a respective beam exit location and focus them to a focal point situated outside the beam exit location, wherein the optical elements include an optical waveguide serving for guidance of the second laser beam, in that at least the two laser-sources are accommodated in a common housing, and in that the optical waveguide extends within the housing at least over a part of its length;
   wherein the optical waveguide includes a photonic transmission fibre having a large modal field,
   wherein at least a portion of the optical waveguide brings about a temporal pulse compression,
   wherein at least the portion of the optical waveguide bringing about the pulse compression is constituted by a photonic hollow-core fibre.

12. The laser apparatus according to claim 11, wherein the first laser-source is an excimer laser and the second laser-source is a fibre laser.

13. The laser apparatus according to claim 11, wherein the second laser-source is arranged in the housing beneath the first laser-source and the optical waveguide is guided upwards within the housing from the second laser-source laterally past the first laser-source.

14. The laser apparatus according to claim 11, wherein the laser pulses generated by the second laser-source 440 have a pulse duration within the femtosecond range and a pulse-stretcher for time-stretching of the laser pulses to pulse lengths longer than 1 picosecond is inserted between the second laser-source and the optical waveguide.

15. An ophthalmic laser apparatus for ablation of corneal material and cutting of ocular tissue of the living eye, the apparatus comprising:
   a housing including a base portion and an arm portion;
   a first laser source positioned within the base portion of the housing, the first laser source generating a first pulsed laser beam having beam properties matched to the ablation of corneal material, the first pulsed laser beam having a wavelength below 300 nm;

a second laser source positioned within the base portion of the housing, the second laser source being separate from the first laser source and generating a second pulsed laser beam having beam properties matched to the making of an incision in the ocular tissue, the second pulsed laser beam having a wavelength above 300 nm;

a plurality of optical elements for guiding the first and second laser beams on separate beam paths to first and second beam exit locations along the arm portion of the housing, the plurality of optical elements including at least a first optical waveguide that guides the second laser beam to the second beam exit location along the arm portion of the housing.

16. The laser apparatus according to claim 15, wherein the first laser-source is an excimer laser and the second laser-source is a fibre laser.

17. The laser apparatus according to claim 15, further comprising a handpiece coupled to the housing by one or more flexible cables, the handpiece including one or more optical elements of the plurality of optical elements.

18. The laser apparatus according to claim 15, further comprising a first beam tube positioned within the arm portion of the housing, the first beam tube configured to guide the first laser beam towards the first beam exit location.

19. The laser apparatus according to claim 18, further comprising a second beam tube positioned within the arm portion of the housing, the second beam tube configured to guide the second laser beam towards the second beam exit location.

20. The laser apparatus according to claim 19, wherein the first optical waveguide extends between the second laser source and the second beam tube.

* * * * *